(12) United States Patent
Gaska et al.

(10) Patent No.: US 7,553,456 B2
(45) Date of Patent: Jun. 30, 2009

(54) ORGANISM GROWTH SUPPRESSION USING ULTRAVIOLET RADIATION

(75) Inventors: Remigijus Gaska, Columbia, SC (US); Yuriy Bilenko, Columbia, SC (US); Michael Shur, Latham, NY (US)

(73) Assignee: Sensor Electronic Technology, Inc., Columbia, SC (US)

( * ) Notice: Subject to any disclaimer, the term of this patent is extended or adjusted under 35 U.S.C. 154(b) by 432 days.

(21) Appl. No.: 11/380,512

(22) Filed: Apr. 27, 2006

(65) Prior Publication Data
US 2007/0205382 A1    Sep. 6, 2007

Related U.S. Application Data

(60) Provisional application No. 60/778,482, filed on Mar. 2, 2006.

(51) Int. Cl.
*A62B 11/00* (2006.01)
(52) U.S. Cl. .................... 422/121; 422/122
(58) Field of Classification Search ............ 422/62, 422/121, 122, 124
See application file for complete search history.

(56) References Cited

U.S. PATENT DOCUMENTS

| | | | |
|---|---|---|---|
| 3,817,703 A | 6/1974 | Atwood | |
| 5,364,645 A | 11/1994 | Lagunas-Solar et al. | |
| 5,919,422 A * | 7/1999 | Yamanaka et al. | 422/121 |
| 6,565,803 B1 | 5/2003 | Bolton et al. | |
| 6,576,188 B1 | 6/2003 | Rose et al. | |
| 6,579,495 B1 | 6/2003 | Maiden | |
| 6,673,137 B1 | 1/2004 | Wen | |
| 6,818,177 B1 | 11/2004 | Turcotte | |
| 7,160,370 B2 | 1/2007 | Baca et al. | |
| 2002/0074559 A1 | 6/2002 | Dowling et al. | |
| 2002/0176809 A1 | 11/2002 | Siess | |
| 2003/0194692 A1 | 10/2003 | Purdum | |
| 2007/0196235 A1 * | 8/2007 | Shur et al. | 422/62 |

OTHER PUBLICATIONS

Elasri et al., "Study of the Response of a Biofilm Bacterial Community to UV Radiation", Appl Environ Microbiol., May 1999, 65(5), pp. 2025-2031.

* cited by examiner

*Primary Examiner*—Kiet T Nguyen
(74) *Attorney, Agent, or Firm*—Hoffman Warnick LLC

(57) ABSTRACT

A solution for suppressing organism growth using ultraviolet radiation generated by solid state ultraviolet radiation emitters, such as ultraviolet diodes is provided. The invention includes a connection structure that includes a plurality of solid state ultraviolet radiation emitters disposed thereon. Each of the plurality of solid state ultraviolet radiation emitters emits ultraviolet radiation having a wavelength less than or equal to four hundred nanometers to harm a target organism that may be present on a surface. In one embodiment, the connection structure comprises a two-dimensional mesh that may be placed adjacent an air filter, incorporated in a cover, and/or moved with respect to a surface, such as the interior of an air duct. In this manner, the invention can suppress and/or prevent the growth of organisms, such as biofilms and mold, in locations that are susceptible to such growth.

24 Claims, 6 Drawing Sheets

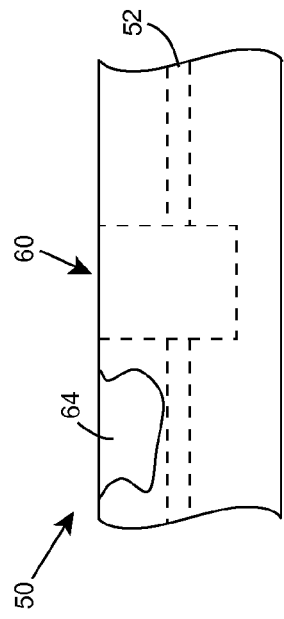
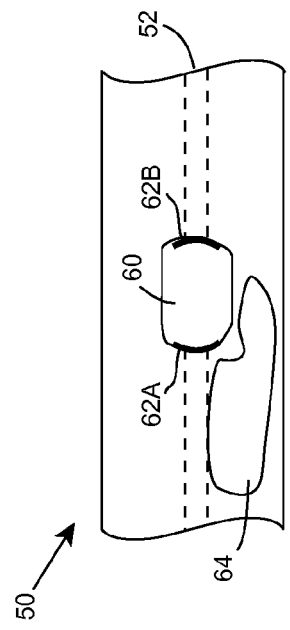
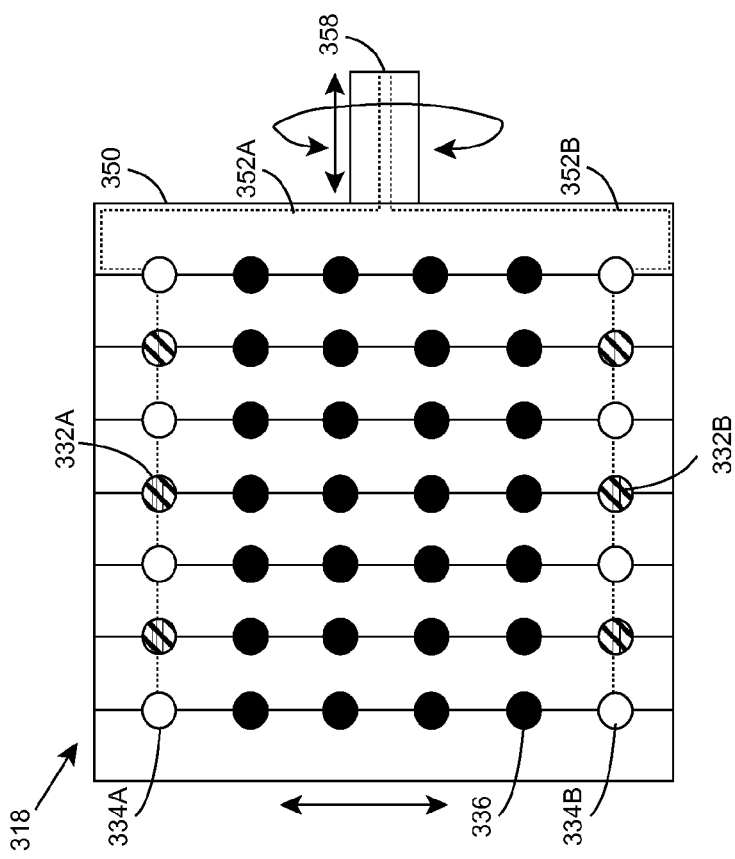

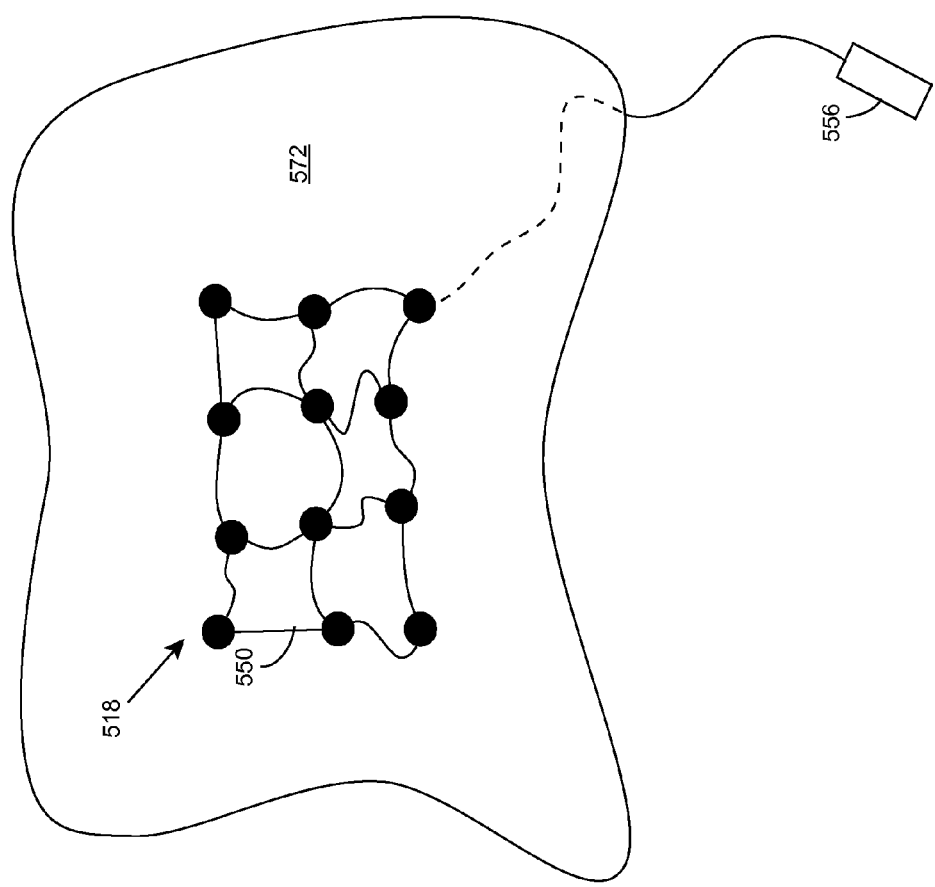

ORGANISM GROWTH SUPPRESSION USING ULTRAVIOLET RADIATION

CROSS-REFERENCE TO RELATED APPLICATIONS

The current application claims the benefit of co-pending U.S. Provisional Application No. 60/778,482, filed on Mar. 2, 2006, which is hereby incorporated herein by reference. The current application is related in some aspects to co-pending U.S. Utility application Ser. No. 11/180,495, filed on Jul. 13, 2005, which is hereby incorporated herein by reference.

FIELD OF THE INVENTION

The invention relates generally to suppressing the growth of organisms, such as biofilm and/or mold, and more particularly, to a solution for suppressing organism growth using ultraviolet radiation generated by solid state ultraviolet radiation emitters, such as ultraviolet diodes.

BACKGROUND OF THE INVENTION

A biofilm is a community of microorganisms, such as bacteria, that are attached to a solid surface. The microorganisms in a biofilm form a matrix structure, and can be highly resistant to antibiotics. Molds can produce various allergens, irritants, and toxic substances, which can cause various health problems. The unwanted growth of organisms such as biofilm and/or mold can be a major problem for various situations. For example, in heating, ventilation, and air conditioning (HVAC) systems, such growth can occur on air filters, the interior of duct work for the air flow, water pipes, and/or the like. Similarly, such growth can occur on various surfaces and utensils within eating establishments, kitchens, bathrooms, hospitals, etc. Infections that at least in part are caused by these organisms account for many otherwise avoidable illnesses and even deaths each year.

Ultraviolet radiation has been shown to damage proteins and membranes in biofilms. Ultraviolet radiation having a longer wavelength (e.g., 320-400 nanometers) may damage cell DNA by creating reactive oxygen compounds, such as $H_2O_2$, $O_2$, etc., which cause single strand breaks in DNA. Ultraviolet radiation having a shorter wavelength (e.g., 290-320 nanometers) is absorbed by DNA and proteins and alters nucleotides, while ultraviolet radiation of a very short wavelength (e.g., 100-290 nanometers) exhibits the strongest germicidal effects.

To this extent, ultraviolet radiation has been successfully used in the purification (e.g., sterilization) of various media, such as air, water, and food. In general, it is desirable that the ultraviolet radiation comprises wavelength(s) that are close to the absorption peak(s) of biologically significant molecules of DNA and/or proteins of a target impurity. For example, impurities, such as a bacterium, a virus, a protozoan, a germ, etc., comprise DNA/proteins having corresponding absorption peaks. By exposing the DNA/proteins to ultraviolet radiation having a wavelength close to the absorption peak(s) for a sufficient time and at a sufficient power, the impurity is destroyed. To this extent, exposing a medium that includes one or more of these impurities to sufficient ultraviolet radiation can destroy some or all of the impurities. When sufficient impurities are destroyed, the medium is purified to a safe condition.

Typically, the source of the ultraviolet radiation in a purification system is a mercury lamp. To this extent, a low-pressure or a medium-pressure mercury lamp provides a linear spectrum of radiation with one or more peak lines having a wavelength that is in the relative vicinity to the DNA absorption line. For example, a low-pressure mercury lamp having a main peak at 253.4 nanometers (nm) is generally used in low-consumption residential water purification systems and residential air purification systems. Further, a medium-pressure mercury lamp having a higher radiation power and a multi-peak radiation spectrum is used in municipal systems with medium and high water consumption.

However, the use of a mercury lamp as the source of ultraviolet radiation has significant drawbacks. For example, mercury is an extremely dangerous element, thereby limiting the applications of mercury-based water and/or air purification systems. In particular, such a mercury-based water purification system is generally not used in transportation or individual applications. Further, a typical lifetime of the mercury lamp generally does not exceed ten thousand hours. Still further, the radiation spectrum of the ultraviolet radiation generated by the mercury lamp includes peak lines having characteristic wavelengths that do not exactly coincide with the absorption peaks of DNA and proteins and these peak lines cannot be controlled or adjusted, which results in a decrease in the efficiency of the system. Still further, mercury lamps are fragile and bulky, which generally adds to the overall cost and/or size of the system and does not allow for a flexible design. Various other limitations are present as will be recognized by one of ordinary skill in the art.

In view of the foregoing, a need exists to overcome one or more of the deficiencies in the related art.

BRIEF SUMMARY OF THE INVENTION

The invention provides a solution for suppressing organism growth using ultraviolet radiation generated by solid state ultraviolet radiation emitters, such as ultraviolet diodes. The invention includes a connection structure that includes a plurality of solid state ultraviolet radiation emitters disposed thereon. Each of the plurality of solid state ultraviolet radiation emitters emits ultraviolet radiation having a wavelength less than or equal to four hundred nanometers to harm (e.g., suppress growth, reduce an amount, kill, damage, injure, etc.) a target organism that may be present on a surface. In one embodiment, the connection structure comprises a two-dimensional mesh that may be placed adjacent an air filter, incorporated in a cover, and/or moved with respect to a surface, such as the interior of an air duct. In this manner, the invention can suppress and/or prevent the growth of organisms, such as biofilms and mold, in locations that are susceptible to such growth.

A first aspect of the invention provides a system for suppressing organism growth, the system comprising: a connection structure; and a plurality of solid state ultraviolet radiation emitters disposed on the connection structure, wherein each of the plurality of emitters emits ultraviolet radiation having a wavelength less than or equal to four hundred nanometers to harm a target organism.

A second aspect of the invention provides a system for suppressing organism growth, the system comprising: a connection structure; a plurality of solid state ultraviolet radiation emitters disposed on the connection structure, wherein each of the plurality of emitters emits ultraviolet radiation having a wavelength less than or equal to four hundred nanometers to harm a target organism; at least one power source that operates the plurality of emitters; and wiring that connects each of the plurality of emitters to at least one of the at least one power sources.

A third aspect of the invention provides a method of suppressing organism growth, the method comprising: obtaining a connection structure comprising a two dimensional mesh that includes a plurality of solid state ultraviolet radiation emitters disposed thereon, wherein each of the plurality of emitters emits ultraviolet radiation having a wavelength less than or equal to four hundred nanometers; placing the connection structure adjacent to a surface; and emitting ultraviolet radiation toward the surface to harm a target organism.

The illustrative aspects of the present invention are designed to solve one or more of the problems herein described and/or one or more other problems not discussed.

BRIEF DESCRIPTION OF THE SEVERAL VIEWS OF THE DRAWINGS

These and other features of the invention will be more readily understood from the following detailed description of the various aspects of the invention taken in conjunction with the accompanying drawings that depict various embodiments of the invention, in which:

FIGS. 3A-C show illustrative examples of the suppression component of FIG. 1 according to several embodiments of the invention.

FIGS. 4A-B show a side view and top view, respectively, of an illustrative connection structure according to an embodiment of the invention.

FIG. 6 shows another illustrative application of a suppression component according to an embodiment of the invention.

It is noted that the drawings are not to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As indicated above, the invention provides a solution for suppressing organism growth using ultraviolet radiation generated by solid state ultraviolet radiation emitters, such as ultraviolet diodes. The invention includes a connection structure that includes a plurality of solid state ultraviolet radiation emitters disposed thereon. Each of the plurality of solid state ultraviolet radiation emitters emits ultraviolet radiation having a wavelength less than or equal to four hundred nanometers to harm (e.g., suppress growth, reduce an amount, kill, damage, injure, etc.) a target organism that may be present on a surface. In one embodiment, the connection structure comprises a two-dimensional mesh that may be placed adjacent an air filter, incorporated in a cover, and/or moved with respect to a surface, such as the interior of an air duct. In this manner, the invention can suppress and/or prevent the growth of organisms, such as biofilms and mold, in locations that are susceptible to such growth. As used herein, unless otherwise noted, the term "set" means one or more (i.e., at least one) and the phrase "any solution" means any now known or later developed solution.

Figure 1:
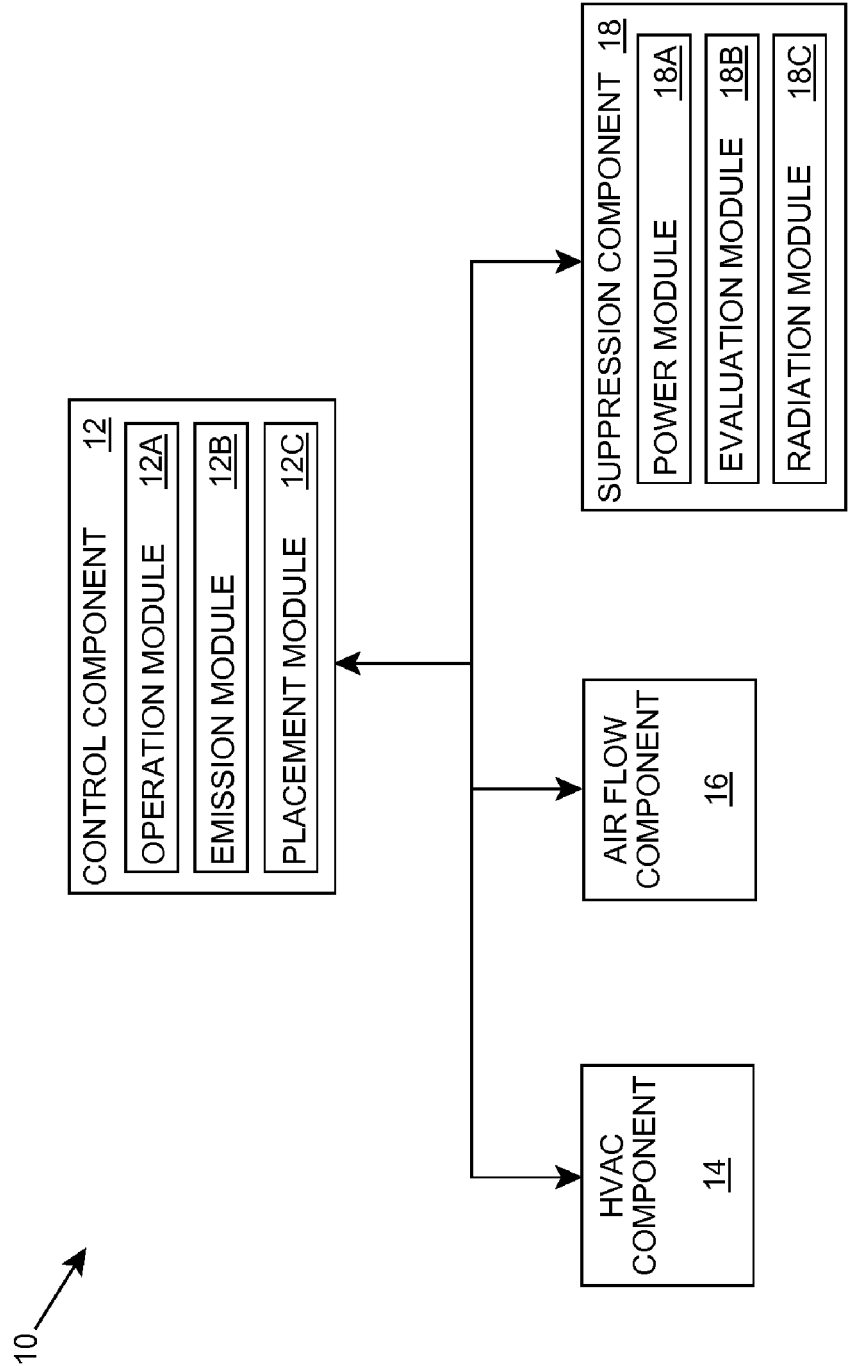
FIG. 1 shows an illustrative system for suppressing organism growth according to an embodiment of the invention.

Turning to the drawings, FIG. 1 shows an illustrative system 10 for suppressing organism growth according to an embodiment of the invention. In general, system 10 comprise a heating, ventilation, and air conditioning (HVAC) system, which can be included in any structure, such as a home, an office building, etc. To this extent, system 10 includes a control component 12, an HVAC component 14, an air flow component 16, and a suppression component 18.

Control component 12 is shown including an operation module 12A, which manages the operation of HVAC component 14 and air flow component 16 using any solution. For example, HVAC component 14 can include one or more sensors (e.g., a temperature sensor, humidity sensor, and/or the like), which provide information on the environment for processing by operation module 12A. In response, operation module 12A can operate a set of subsystems (e.g., a heater, an air conditioner, a humidifier, and/or the like) of HVAC component 14 to maintain a desired environment within the structure (e.g., temperature, humidity, and/or the like). Further, in order to circulate conditioned air throughout the structure, control component 12 can operate a set of subsystems (e.g., fan, blower, damper, deflector, and/or the like) of air flow component 16 using any solution. To this extent, air flow component 16 can include various ducts that deliver the conditioned air from HVAC component 14 to one or more locations within the structure as well as various ducts that return air to HVAC component 14 from various locations within the structure as is known in the art.

Control component 12 is further shown including an emission module 12B and a placement module 12C, both of which manage one or more aspects of suppression component 18. Suppression component 18 comprises one or more structures for suppressing organism growth (e.g., by eliminating/destroying existing organism(s), preventing the growth of the organism(s), and/or the like). As discussed herein, suppression component 18 can suppress the growth of a target organism, such as biofilm or mold. However, it is understood that the teachings of the invention can be applied to any undesired organism, the growth of which can be suppressed using suppression component 18.

Figure 2:
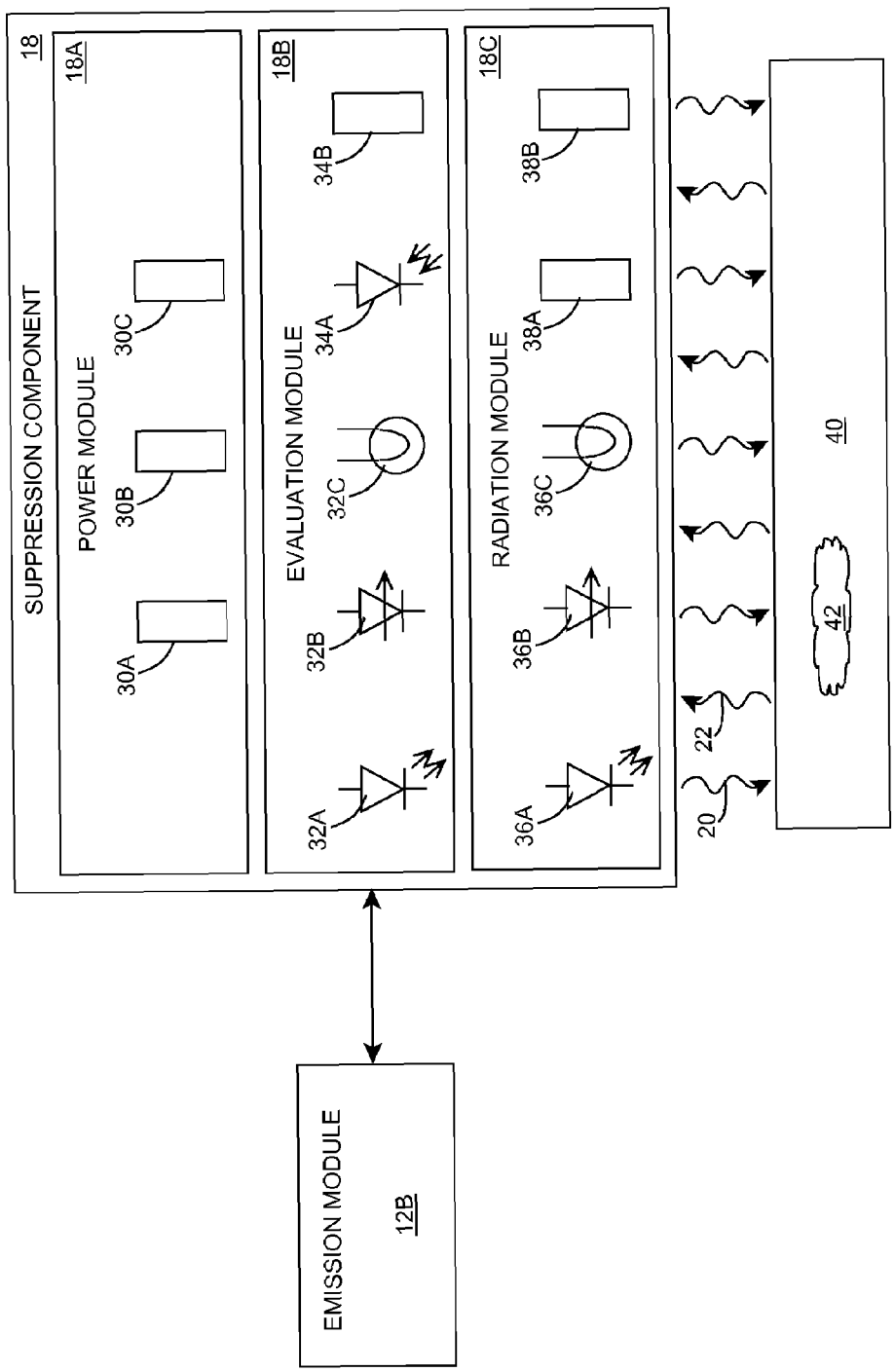
FIG. 2 shows a more detailed view of the suppression component of FIG. 1 according to an embodiment of the invention.

In any event, suppression component 18 is shown including a power module 18A, an evaluation module 18B, and a radiation module 18C. FIG. 2 shows a more detailed view of suppression component 18 according to an embodiment of the invention. In general, power module 18A includes a set of power sources 30A-C, which provide power to one or more devices in evaluation module 18B and/or radiation module 18C. Power sources 30A-C can comprise a conventional source of power (e.g., a battery), in which case suppression component 18 can be implemented as an independent system. Further, power sources 30A-C can comprise one or more devices for regulating the flow of power (e.g., a switch), in which case a source of power can be implemented apart from power module 18A. Still further, emission module 12B can communicate with power module 18A to control operation of one or more power sources 30A-C to manage suppression component 18. Emission module 12B can communicate with power module 18A using any solution (e.g., any combination of wired and/or wireless transmission techniques).

In this manner, emission module 12B can selectively operate one or more of the devices in evaluation module 18B and/or radiation module 18C by adjusting the operation of power source(s) 30A-C. For example, emission module 12B can turn off one or more devices when they are not required to operate and/or adjust one or more operational characteristics (e.g., power dose, wavelength, etc.) of evaluation module 18B and/or radiation module 18C. To this extent, power module 18A can include one or more power source(s) 30A-C that can: vary an amount of power provided and/or can vary a number of devices to which power is supplied (e.g., to adjust an intensity of the resulting ultraviolet radiation); operate one or more devices in a continuous wave regime; operate one or more devices in a pulsed regime; and/or the like.

Evaluation module 18B can include a set of devices that can measure a presence and/or an amount of one or more target organisms 42, which may be present/growing on surface 40. To this extent, evaluation module 18B can include any combination of one or more ultraviolet radiation sources 32A-C (e.g., ultraviolet light emitting diode 32A, ultraviolet laser 32B, ultraviolet mercury lamp 32C, and/or the like) and/or one or more terahertz radiation sources and the corresponding sensing devices 34A-B (e.g., photodiode 34A, photodetector 34B, and/or the like). The radiation source(s) 32A-C can emit radiation 20 towards surface 40 and/or organism 42 and the sensing device(s) 34A-C can identify the presence and/or amount of organism(s) 42 based on a sensed reflection of radiation 22. In one embodiment, power module 18A includes one or more components that obtain the sensed data from evaluation module 18B and provide the data for processing by emission module 12B. Emission module 12B can identify the presence and/or amount of organism(s) 42 based on the sensed data and operate suppression component 18 accordingly.

Radiation module 18C includes a set of devices that can emit ultraviolet radiation 20 to harm target organism 24. To this extent, radiation 20 emitted by radiation module 18C can comprise a wavelength less than or equal to four hundred nanometers. In one embodiment, the set of ultraviolet radiation sources 36A-C comprises exclusively of a set of solid state ultraviolet radiation emitters. To this extent, the set of ultraviolet radiation sources 36A-C can include ultraviolet diodes 36A-B, such as an ultraviolet light emitting diode 36A an ultraviolet laser diode 36B, and/or the like. Each ultraviolet diode 36A-B can comprise any type of ultraviolet radiation emitting diode, such as a semiconductor light emitting diode, a compound semiconductor diode (e.g., AlInGaN/GaN), a nitride-based semiconductor ultraviolet light emitting diode, a periodic array of ultraviolet diodes, and/or the like. In this manner, no mercury is required in radiation module 18C. However, in another embodiment, radiation module 18C can include one or more mercury lamps 36C, such as a low-pressure and/or medium-pressure mercury lamp, which can provide an increased power dose over a linear spectrum. In any event, the ultraviolet radiation 20 generated by radiation module 18C can comprise one or more wavelength bands that coincide with or are close to the absorption spectra of one or more targeted organism(s) 42.

The use of solid state ultraviolet radiation emitters, such as ultraviolet light emitting diode(s) 32A, 36A and/or ultraviolet laser diode(s) 32B, 36B provides various benefits. For example, diodes 36A and/or 36B can generate ultraviolet radiation having one or more wavelength bands that coincide with or are close to the absorption spectra of a target organism(s) 42. In one embodiment, a predominant wavelength of a radiation band generated by diodes 36A and/or 36B can be adjusted, e.g., by adjusting the power provided by power module 18A, by selecting a particular subset of radiation sources 36A-C that generate ultraviolet radiation having the desired wavelength, adjusting a band gap of the active layers of a set of ultraviolet sources 36A-B to adjust the generated wavelength, and/or the like.

To this extent, diodes 36A and/or 36B could generate ultraviolet radiation 20 having a wavelength band that can be adjusted by emission module 12B based on the target organism 42 and its corresponding absorption spectra. For example, the wavelength band could be adjusted between approximately 100 nanometers and approximately 350 nanometers. In one embodiment, the wavelength band is adjusted between approximately 200 nanometers and approximately 350 nanometers. Similarly, a power dose for the ultraviolet radiation 20 generated by radiation module 18C, e.g., diodes 36A and/or 36B, can be adjusted by emission module 12B based on one or more properties of organism 42 (e.g., an amount of organism 42) and/or surface 40 (e.g., a distance, a contour, a relative motion, etc.). In one embodiment, the power dose can be adjusted to be between approximately 3.5 micro-Joules per square centimeter ($\mu J/cm^2$) and approximately 1000 milli-Joules per square centimeter ($mJ/cm^2$).

Additionally, radiation module 18C can combine ultraviolet radiation suppression with one or more solutions that emit non-ultraviolet radiation 20. To this extent, radiation module 18C can comprise a set of non-ultraviolet radiation sources 38A-B, which can comprise an X-ray radiation source, an ionizing radiation source, a visible radiation source (e.g., a white light emitting diode), and/or the like. Operation of non-ultraviolet radiation sources 38A-B can be managed by emission module 12B in conjunction with power module 18A in a similar manner as discussed herein with respect to ultraviolet radiation source(s) 36A-C.

Further, evaluation module 18B can include a set of devices that can obtain data on an environment within which suppression component 18 is disposed. Emission module 12B can use the environment data to adjust operation of radiation module 18C. For example, evaluation module 18B can obtain data on an air flow. In this case, emission module 12B can adjust a current (and therefore an output power) applied to radiation module 18C based on the air flow (e.g., a higher air flow enables improved cooling of the devices, enabling a higher current). Still further, evaluation module 18B can sense an amount of ultraviolet radiation 20 output by radiation module 18C, which emission module 12B can use as part of a control feedback loop to provide a desired sterilization dose.

Figure 3A:
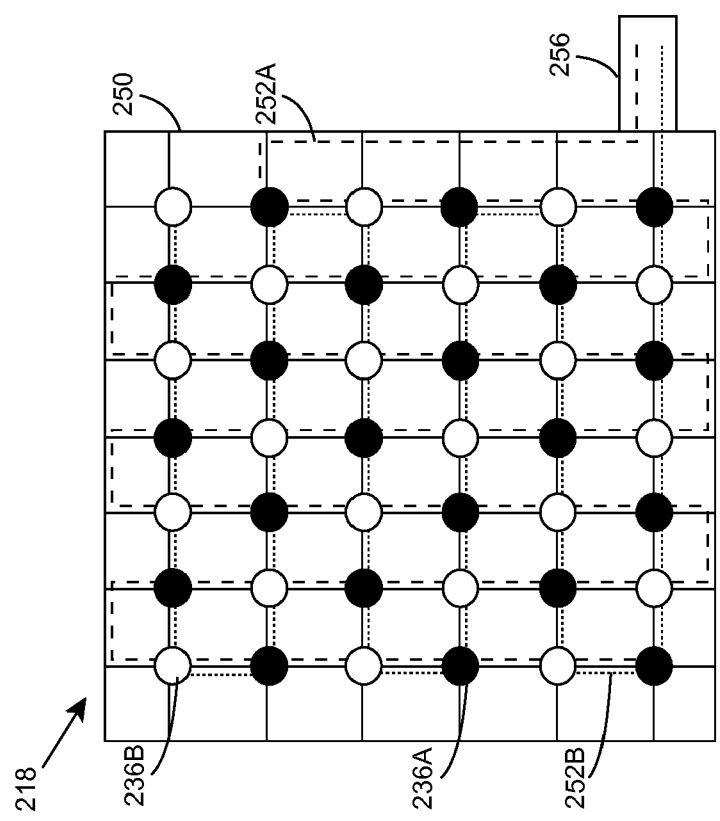
Figure 3B:
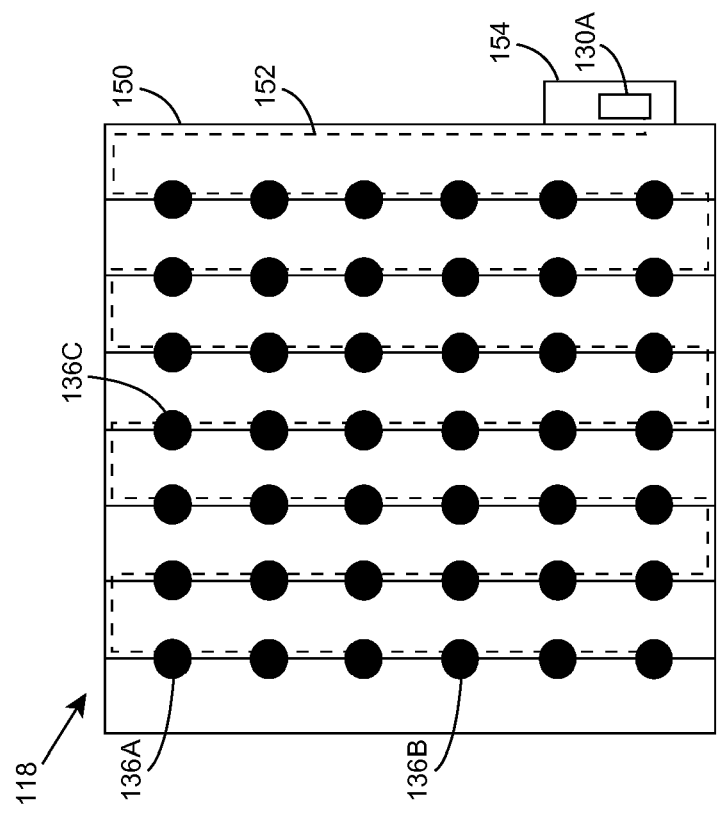

FIGS. 3A-C show illustrative examples of suppression component 18 (FIG. 1) according to several embodiments of the invention. In FIG. 3A, suppression component 118 is shown including a connection structure 150, which includes a plurality of ultraviolet diodes, such as ultraviolet diodes 136A-C. Connection structure 150 comprises a two dimensional mesh, which can be formed of a flexible wire, a rigid wire, a flexible plastic, a rigid plastic, and/or the like. Connection structure 150 includes wiring 152, which electrically connects each ultraviolet diode 136A-C to a power source 130A shown in an enclosure 154. In one embodiment, connection structure 150 is made of the wiring 152 (e.g., flexible and/or rigid). Alternatively, some or all of connection structure 150 can comprise an alternative material, such as a flexible or rigid plastic, that includes the wiring 152 (e.g., disposed in a hollow interior of connection structure 150).

In any event, suppression component 118 comprises an embodiment in which each ultraviolet diode 136A-C is operated using a single power source 130A (e.g., a battery). In this case, suppression component 118 can operate autonomously, and therefore be implemented independent of the other components shown in system 10 (FIG. 1). Additionally, power source 130A can include a switch or the like, that enables a user to selectively turn on and off ultraviolet diodes 136A-C.

FIG. 3B shows an alternative illustrative embodiment of suppression component 218, in which connection structure 250 includes a first wiring 252A that electrically connects a first set of ultraviolet diodes, such as ultraviolet diode 236A, and a second wiring 252B that electrically connects a second set of ultraviolet diodes, such as ultraviolet diode 236B. In this case, each set of ultraviolet diodes 236A-B can be independently operated from the other set. For example, each ultraviolet diode in one set of ultraviolet diodes, e.g., ultraviolet diode 236A, could emit electromagnetic radiation having a first predominant wavelength (e.g., 250-280 nanometers), while each ultraviolet diode in the other set of ultraviolet diodes, e.g., ultraviolet diode 236B, could emit electromagnetic radiation having a second predominant wavelength (e.g., 280-300 nanometers) that is distinct from the first predominant wavelength. In this case, the first and second wavelengths could be selected based on a target organism 42 (FIG. 2). It is understood that each set of ultraviolet diodes 236A-B could emit electromagnetic radiation having wavelength(s) that are entirely distinct or include some overlap from the electromagnetic radiation emitted by the other set(s) of ultraviolet diodes 236A-B.

Suppression component 218 includes an interface 256 that enables wirings 252A-B to be electrically connected to power module 18A (FIG. 2) and/or emission module 12B (FIG. 2). For example, interface 256 can comprise a male connector that can be electrically connected to a female connector as is known. However, it is understood that interface 256 can comprise any solution for electrically connecting wirings 252A-B to power module 18A.

The use of two distinct wirings 252A-B, one for each set of ultraviolet diodes 236A-B, enables emission module 12B to independently operate the sets of ultraviolet diodes 236A-B. For example, emission module 12B could use only one set of ultraviolet diodes 236A-B based on a type and/or amount of a target organism 42 (FIG. 2) that was measured by evaluation module 18B (FIG. 2). In particular, emission module 12B could use a single set of ultraviolet diodes to emit a lower intensity ultraviolet radiation 20 (FIG. 2) when a small amount of a target organism 42 is measured, but use both sets of ultraviolet diodes to emit a higher intensity ultraviolet radiation 20 when a sufficiently large amount of target organism 42 is measured. Further, the electrical characteristics of the operation of each set of ultraviolet diodes 236A-B could be different, e.g., power module 18A (FIG. 2) could operate one set of ultraviolet diodes in a pulsed regime, while emission module 12B operates the other set of ultraviolet diodes in a continuous wave regime.

FIG. 3C shows still another illustrative embodiment of suppression component 318, in which connection structure 350 includes a location structure 358. Location structure 358 enables placement module 12C to position suppression component 318 in a desired location. To this extent, location structure 358 can enable horizontal and/or vertical movement of suppression component 318, e.g., along surface 40 (FIG. 2). Further, location structure 358 can enable clockwise and/or counter clockwise rotation of connection structure 350 with respect to a primary illumination direction of ultraviolet diodes 336. In one embodiment, location structure 358 can comprise a wheeled/tracked vehicle or the like that supports suppression component 318, and which placement module 12C can operate using any wired and/or wireless communication solution.

Suppression component 318 further includes wirings 352A-B for independently operating two sets of devices implemented as part of evaluation module 18B (FIG. 2). In this case, emission module 12B (FIG. 2) can operate one set of devices, such as ultraviolet diode 332A and sensing device 334A, to evaluate an untreated surface 40 (FIG. 2). Based on the evaluation, emission module 12B can operate the set of ultraviolet diodes 336 accordingly to suppress the growth of any organism(s) 42, which are measured. Emission module 12B can operate the second set of devices, such as ultraviolet diode 332B and sensing devices 334B, to evaluate surface 40 after treatment in order to provide feedback on its effectiveness. Based on the feedback, placement module 12C (FIG. 1) could relocate suppression component 318 for further processing of the same area of surface 40 and/or move on to a new area of surface 40.

While each of the illustrative connection structures of FIGS. 3A-C is shown having a substantially rectangular shape with devices located in rows/columns, it is understood that each connection structure can comprise any shape with devices located in any configuration. For example, the connection structure could comprise a one dimensional row of devices, a three dimensional configuration of devices, devices disposed in a circular/partially circular manner, etc. Further, illustrative aspects of each of the various embodiments can be combined to generate a connection structure according to the invention. Still further, other variations of connection structures obvious to one in the art, but not expressly shown and discussed herein are within the scope of the invention.

In any event, FIGS. 4A-B show a side view and top view, respectively, of an illustrative connection structure 50 according to an embodiment of the invention. In particular, an illustrative solution for electrically connecting the various devices of suppression component 18 (FIG. 2) is shown. In this case, connection structure 50 comprises a structure, such as a rigid or flexible plastic, which includes wiring 52 therein for electrically connecting each device. A device can be connected to wiring 52 by insertion into an aperture 60 in the structure. The aperture can include contacts 62A-B that are disposed in such a manner as to contact and provide an electrical connection to corresponding contacts 62A-B on the device. In this manner, the various devices can be replaced, such as when a different device is desired, a device breaks down, and/or the like.

Connection structure 50 is also shown having a germicidal catalyst 64 disposed thereon. The germicidal catalyst can be included to further encourage the suppression/destruction of a target organism 42 (FIG. 2). The germicidal catalyst can comprise any type of germicidal catalyst, such as silicon carbide, titanium dioxide, and/or the like, and can be selected based on its effectiveness against a particular target organism 42 (e.g., biofilm, mold, etc.).

Figure 5:
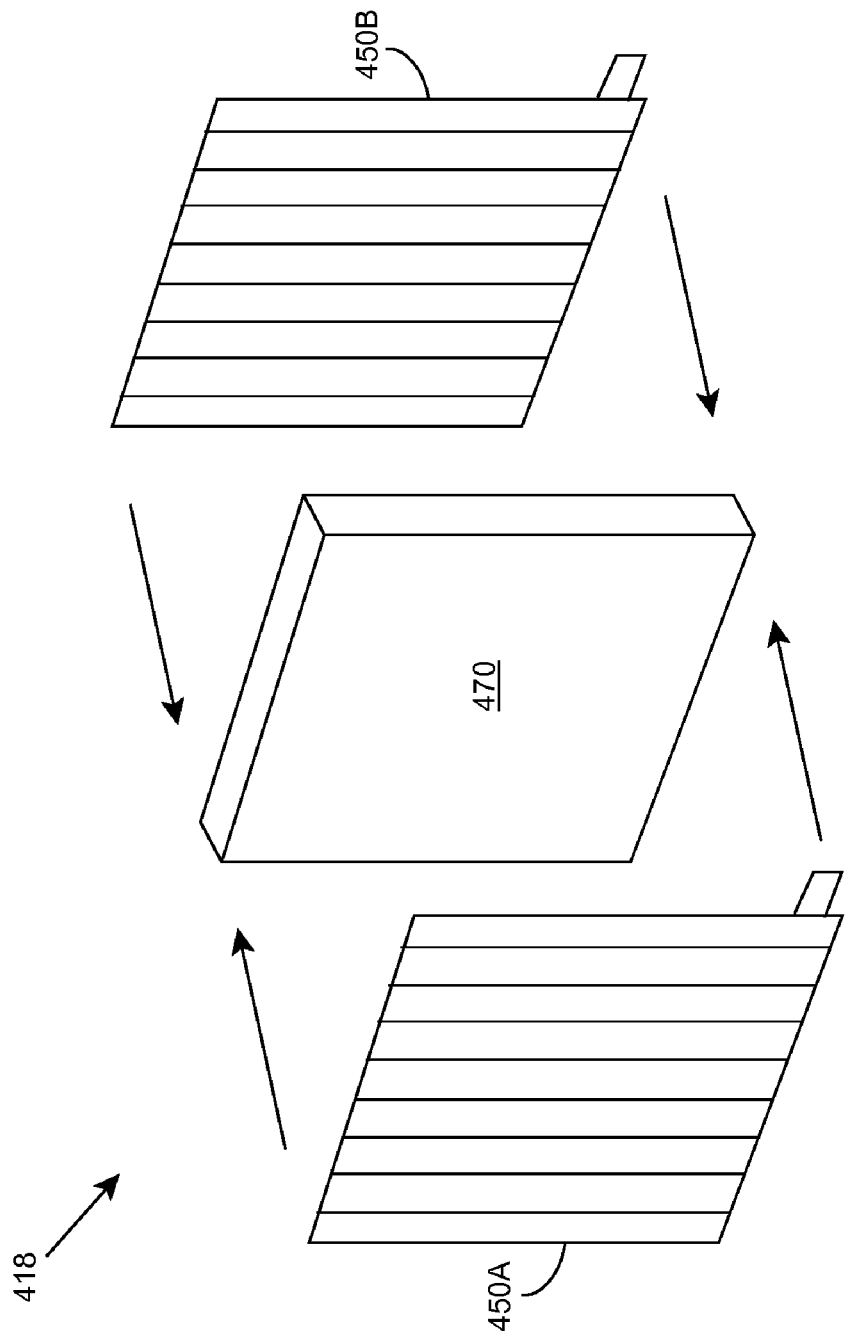
FIG. 5 shows an illustrative application of a suppression component according to an embodiment of the invention.

FIG. 5 shows an illustrative application of a suppression component 418 according to an embodiment of the invention. In particular, suppression component 418 includes two connection structures 450A-B, each of which is located adjacent to an air filter 470 on opposing sides of air filter 470. Each connection structure 450A-B can be permanently and/or temporarily attached to air filter 470 and/or the other connection structure 450A-B using any solution. In one embodiment, each connection structure 450A-B is temporarily attached to air filter 470, thereby enabling air filter 470 to be periodically replaced. In any event, each connection structure 450A-B can include a set of ultraviolet diodes that emit ultraviolet radiation that is directed toward air filter 470. In this manner, the growth of organism(s) 42 (FIG. 2) can be suppressed/prevented on the corresponding adjacent surfaces 40 (FIG. 2) of air filter 470. It is understood that while two connection structures 450A-B are shown, an application could use only a single connection structure in conjunction with air filter 470. Further, it is understood that each connection structure 450A-B can include any combination of the various modules of suppression component 418 as discussed herein.

FIG. 6 shows another illustrative application of a suppression component 518 according to an embodiment of the invention. In this case, a flexible connection structure 550 for suppression component 518 is incorporated into a cover, such as flexible covering 572. Flexible connection structure 550 can comprise flexible plastic, flexible wiring, and/or the like.

Flexible covering 572 can comprise any of various types of coverings, such as a tool cover (e.g., for surgical tools), a blanket, a wipe, and/or the like. Further flexible covering 572 could comprise a covering for generally flat surfaces, such as a wall cover, a floor cover, a ceiling cover, a table cover (e.g., a surgical table), and/or the like. However, it is understood that in the latter case, connection structure 550 could be implemented in a rigid covering, and not in a flexible covering 572 as shown. In any event, flexible covering 572 can be placed adjacent to a surface 40 (FIG. 2) for which the suppression of the growth of organism(s) 42 (FIG. 2) is desired. To this extent, flexible covering 572 can be placed in such a manner that radiation emitted from the various devices included in suppression component 518 is directed towards the adjacent surface 40. Operation of the various devices can be managed via an interface 556 or the like as discussed herein.

Returning to FIG. 1, as described herein, control component 12 can control HVAC component 14, air flow component 16, and/or suppression component 18. To this extent, it is understood that control component 12 includes one or more input/output (I/O) devices for communicating with the various components 14, 16, 18. Further, control component 12 can include I/O device(s) for communicating with a user and/or one or more additional component not shown. Communications between the various component can occur over any combination of one or more types of wired and/or wireless communications links, such as a public or private network. Regardless, control component 12 can comprise any computing article of manufacture capable of implementing the process described herein. For example, control component 12 can comprise one or more general purpose computing articles of manufacture capable of executing computer program code installed thereon. In this case, the functionality described in conjunction with each module 12A-C can be enabled by computer program code.

However, it is understood that general purpose computing device(s) and program code is only representative of various possible equivalent computing devices that may perform the process described herein. To this extent, in other embodiments, the functionality described herein can be implemented by one or more computing articles of manufacture that include any combination of general and/or specific purpose hardware and/or computer program code. In each embodiment, the program code and hardware can be created using standard programming and engineering techniques, respectively.

In any event, when control component 12 includes computer program code, it is understood that various sub-components, such as a memory and processor, are included to enable the execution thereof. As used herein, it is understood that the terms "program code" and "computer program code" are synonymous and mean any expression, in any language, code or notation, of a set of instructions intended to cause a computing device having an information processing capability to perform a particular function either directly or after any combination of the following: (a) conversion to another language, code or notation; (b) reproduction in a different material form; and/or (c) decompression. To this extent, program code can be embodied as one or more types of program products, such as an application/software program, component software/a library of functions, an operating system, a basic I/O system/driver for a particular computing and/or I/O device, and the like. Further, program code can be stored in a computer-readable medium, which comprises one or more of any type of tangible medium of expression (e.g., physical embodiment) of the program code.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A system for suppressing organism growth, the system comprising:
    a connection structure, wherein the connection structure is a two dimensional mesh; and
    a plurality of solid state ultraviolet radiation emitters periodically disposed on the connection structure in a two dimensional pattern, wherein each of the plurality of emitters emits ultraviolet radiation having a wavelength less than or equal to four hundred nanometers to harm a target organism.

2. The system of claim 1, wherein the connection structure comprises at least one of: a flexible wire, a rigid wire, a flexible plastic, or a rigid plastic.

3. The system of claim 1, wherein the plurality of emitters includes at least one of: a light emitting diode or a laser diode.

4. The system of claim 1, further comprising a power source that operates the plurality of emitters.

5. The system of claim 1, further comprising a germicidal catalyst disposed on the connection structure.

6. The system of claim 1, wherein the plurality of emitters includes:
    a first plurality of emitters that emit electromagnetic radiation having a first wavelength; and
    a second plurality of emitters that emit electromagnetic radiation having a second wavelength that is distinct from the first wavelength, wherein the emitters in the first plurality of emitters are interspersed with the emitters in the second plurality of emitters throughout the two dimensional mesh.

7. The system of claim 1, further comprising a mercury lamp that emits ultraviolet radiation having a wavelength less than or equal to four hundred nanometers.

8. The system of claim 1, further comprising a system for moving the connection structure with respect to a surface on which the target organism is present.

9. The system of claim 1, further comprising:
    a system for measuring an amount of the target organism on a surface; and
    a system for adjusting at least one of an intensity or a wavelength of the ultraviolet radiation based on the measured amount of the target organism.

10. The system of claim 9, wherein the system for measuring includes:
    a plurality of emitting devices configured to emit evaluation radiation directed towards the surface;
    a plurality of sensing devices configured to sense a reflection of the evaluation radiation from the surface, wherein the plurality of emitting devices and the plurality of sensing devices are periodically disposed on the connection structure; and
    an evaluation module configured to measure the amount of the target organism on the surface based on the sensed evaluation radiation.

11. The system of claim 1, further comprising an air filter adjacent to the connection structure.

12. The system of claim 1, further comprising a cover that incorporates the connection structure.

13. The system of claim 1, wherein the target organism comprises at least one of: biofilm or mold.

14. A system for suppressing organism growth, the system comprising:
a connection structure;
a plurality of solid state ultraviolet radiation emitters periodically disposed on the connection structure in a two dimensional pattern, wherein each of the plurality of emitters emits ultraviolet radiation having a wavelength less than or equal to four hundred nanometers to harm a target organism, and wherein the plurality of emitters include a first plurality of emitters and a second plurality of emitters interspersed with the first plurality of emitters throughout the connection structure;
at least one power source that operates the plurality of emitters; and
wiring that connects each of the plurality of emitters to at least one of the at least one power source, wherein the at least one power source and the wiring are configured to enable independent operation of the first plurality of emitters and the second plurality of emitters.

15. The system of claim 14, further comprising a system for moving the connection structure with respect to a surface on which the target organism is present.

16. The system of claim 14, further comprising:
a system for measuring an amount of the target organism on a surface; and
a system for adjusting at least one of an intensity or a wavelength of the ultraviolet radiation based on the measured amount of the target organism.

17. The system of claim 14, further comprising an air filter adjacent to the connection structure.

18. The system of claim 14, further comprising a cover that incorporates the connection structure.

19. A method of suppressing organism growth, the method comprising:
obtaining a connection structure comprising a two dimensional mesh that includes a plurality of solid state ultraviolet radiation emitters periodically disposed thereon in a two dimensional pattern, wherein each of the plurality of emitters emits ultraviolet radiation having a wavelength less than or equal to four hundred nanometers;
placing the connection structure adjacent to a solid surface; and
emitting ultraviolet radiation with the plurality of emitters toward the surface to harm a target organism.

20. The method of claim 19, wherein the placing includes moving the connection structure with respect to a fixed surface on which the target organism is present.

21. The method of claim 19, wherein the placing includes attaching an air filter to the connection structure, wherein the surface is on the air filter.

22. The method of claim 19, wherein the placing includes covering the surface with a cover that incorporates the two dimensional mesh.

23. The method of claim 19, further comprising measuring an amount of the target organism on the surface after the placing, wherein the emitting is adjusted based on the measured amount of the target organism.

24. The method of claim 19, wherein the plurality of emitters include a first plurality of emitters and a second plurality of emitters interspersed with the first plurality of emitters throughout the connection structure, and wherein the emitting includes independently operating the first plurality of emitters and the second plurality of emitters.

* * * * *